United States Patent
Choi et al.

(10) Patent No.: US 9,314,212 B2
(45) Date of Patent: Apr. 19, 2016

(54) X-RAY IMAGING APPARATUS

(75) Inventors: Heung-San Choi, Seoul (KR); Jin-Su Kim, Seoul (KR); Jung-Hoon Song, Anyang-si (KR)

(73) Assignee: MORPHEUS CO., LTD., Seoul (KR)

( * ) Notice: Subject to any disclaimer, the term of this patent is extended or adjusted under 35 U.S.C. 154(b) by 331 days.

(21) Appl. No.: 14/117,032

(22) PCT Filed: May 10, 2012

(86) PCT No.: PCT/KR2012/003664
§ 371 (c)(1),
(2), (4) Date: Jan. 13, 2014

(87) PCT Pub. No.: WO2012/153990
PCT Pub. Date: Nov. 15, 2012

(65) Prior Publication Data
US 2014/0334599 A1    Nov. 13, 2014

(30) Foreign Application Priority Data

May 12, 2011   (KR) .......................... 10-2011-0044495

(51) Int. Cl.
| | |
|---|---|
| *A61B 6/00* | (2006.01) |
| *G01N 23/04* | (2006.01) |
| *G21K 5/08* | (2006.01) |
| *G21K 5/10* | (2006.01) |
| *A61B 6/02* | (2006.01) |
| *A61B 6/14* | (2006.01) |
| *A61B 5/00* | (2006.01) |

(52) U.S. Cl.
CPC ................. *A61B 6/02* (2013.01); *A61B 5/0035* (2013.01); *A61B 5/0077* (2013.01); *A61B 6/14* (2013.01); *A61B 6/4411* (2013.01); *A61B 6/4417* (2013.01); *A61B 6/501* (2013.01); *A61B 6/5247* (2013.01)

(58) Field of Classification Search
USPC ......... 378/62, 64, 68, 87, 145, 146, 193, 196, 378/197, 210; 250/370.08, 370.09, 526
See application file for complete search history.

(56) References Cited

U.S. PATENT DOCUMENTS

| | | | | |
|---|---|---|---|---|
| 6,999,555 | B2 * | 2/2006 | Morf ...................... | A61B 6/032 378/62 |
| 8,052,325 | B2 * | 11/2011 | Hibino .................... | A61B 6/04 378/197 |
| 8,582,720 | B2 * | 11/2013 | Morton ................ | G01V 5/0008 378/57 |
| 9,128,198 | B2 * | 9/2015 | Morton ................ | G01V 5/0008 1/1 |
| 2005/0058237 | A1 * | 3/2005 | Morf ...................... | A61B 6/032 378/4 |
| 2010/0054423 | A1 * | 3/2010 | Noda .................... | A61B 6/4441 378/197 |
| 2010/0296626 | A1 * | 11/2010 | Hibino .................... | A61B 6/04 378/44 |
| 2011/0012014 | A1 * | 1/2011 | Livne .................... | A61B 6/032 250/252.1 |
| 2012/0134473 | A1 * | 5/2012 | Morton ................ | G01V 5/0008 378/87 |
| 2014/0133629 | A1 * | 5/2014 | Morton ................ | G01V 5/0008 378/87 |

(Continued)

*Primary Examiner* — Bernard E Souw

(57) ABSTRACT

The present invention relates to an X-ray imaging apparatus, comprising: an X-ray imager including an X-ray beam generator for emitting an X-ray beam, an X-ray beam detector for detecting the X-ray beam to obtain an X-ray image of an object, and a main body unit in which the X-ray beam generator and the X-ray beam detector are installed; and a three-dimensional scanner arranged in the X-ray imager in order to obtain an image of the outer appearance of the object. According to the present invention, an X-ray image and an image of the outer appearance of an object, for example, an image of the skull and an image of the face, can be obtained at the same time, thereby minimizing image correction procedures for matching two images.

10 Claims, 9 Drawing Sheets

(56) References Cited

U.S. PATENT DOCUMENTS

| | | | | |
|---|---|---|---|---|
| 2014/0177799 A1* | 6/2014 | Noda | ............... | G01N 23/04 378/62 |
| 2014/0247918 A1* | 9/2014 | Kang | ............... | A61B 6/4452 378/62 |
| 2014/0321612 A1* | 10/2014 | Schafer | ............... | A61B 6/032 378/41 |
| 2015/0305696 A1* | 10/2015 | Yamakawa | ............... | A61B 6/14 378/19 |

* cited by examiner

200a

X-RAY IMAGING APPARATUS

FIELD OF THE INVENTION

The present invention relates to an X-ray imaging apparatus, and particularly to an X-ray imaging apparatus comprising an X-ray imager and a three-dimensional scanner to obtain an X-ray image together with an exterior image of an object.

BACKGROUND

Imaging techniques using radioactive rays, particularly X-rays, are one of the important techniques employed in the medical fields to acquire internal body images, and X-ray imaging apparatuses use such X-rays.

Conventional X-ray imaging apparatuses using X-rays are put into practice as various types of apparatuses for taking images of all or part of a human body such as internal organs, dental structure and skull.

The conventional X-ray imaging apparatuses are configured to include an X-ray beam generator for emitting and irradiating an X-ray beam on an object, an X-ray beam detector for detecting the X-ray beam that has been irradiated from the X-ray beam generator and then projected on the object placed in the beam path, and an image display unit for displaying the image of the object according to a signal detected in the X-ray beam detector.

Here, the X-ray beam generator and X-ray beam detector are disposed at the locations spaced apart from each other by a predetermined distance. Further, the X-ray beam generator is configured to include an X-ray beam source for emitting the X-ray beam.

One example of the conventional X-ray imaging apparatuses is a dental CT (computed tomography) apparatus, which is an X-ray imaging apparatus used in dental clinics to image teeth and/or skull and provide X-ray images for dental procedures such as orthodontic treatment or maxillary correction. FIG. 1a shows a teeth image taken by the dental CT apparatus and FIG. 1b shows a skull image.

In the X-ray images, facial skin tissues form relatively transparent contours compared to osseous tissues due to the difference in X-ray absorption. The above X-ray imaging apparatuses are used in a variety of fields such as dentistry as mentioned above, as well as plastic surgery. In particular, the field of dentistry or plastic surgery requires not only the above-described X-ray image but also an exterior image of an object, e.g., a face image of a patient for dental correction or plastic surgery.

The exterior image of the object is superimposed with the X-ray image of the corresponding part so that they may be utilized as diagnostic data for the dental correction or plastic surgery and at the same time used to plan the procedures suitable for the patient and simulate a virtual plastic surgery or a virtual correction.

The exterior image of the object needs to be correctly superimposed with the X-ray image of the part corresponding to the exterior image so as to increase accuracy of the diagnostic data. Therefore, the inventors have developed an X-ray imaging apparatus which may increase accuracy of superimposition of an exterior image and an X-ray image of an object and minimize image adjustment procedures for the X-ray image and/or exterior image.

SUMMARY OF THE INVENTION

One object of the present invention is to provide an X-ray imaging apparatus equipped with a scanner, which may increase accuracy of superimposition of an X-ray image (e.g., an image of skeleton such as skull) and an exterior image of an object.

Another object of the present invention is to provide an X-ray imaging apparatus and a three-dimensional scanner for the same, wherein the three-dimensional scanner may be mounted or attached to an X-ray imager.

According to one aspect of the present invention to achieve the objects as described above, there is provided an X-ray imaging apparatus comprising: an X-ray imager comprising an X-ray beam generator for emitting an X-ray beam, an X-ray beam detector for detecting the X-ray beam to obtain an X-ray image of an object, and a body unit to which the X-ray beam generator and X-ray beam detector are mounted; and a three-dimensional scanner being arranged on the X-ray imager to obtain an exterior image of the object.

According to the present invention, the scanner may be removably mounted to the X-ray imager.

The scanner may comprise a scanner body to take the exterior image of the object, and a coupler to fix the scanner body to the X-ray imager.

Herein, the coupler is removably coupled to at least one of the X-ray imager and scanner body.

The body unit comprises a base body to support the weights of the X-ray beam generator and X-ray beam detector, and a support arm arranged on the base body to which the X-ray beam generator and X-ray beam detector are installed.

Herein, the scanner may be supported by the support arm. The X-ray beam detector is removably mounted to the support arm, and the scanner may be removably installed at the location where the X-ray beam detector is mounted.

On the other hand, the body unit may further comprise a scanner arm to which the scanner is mounted. The scanner arm is arranged on the support arm or the base body. Further, the support arm may be configured to rotate around the object.

The scanner may be configured as a three-dimensional (3D) scanner to obtain a three-dimensional image. Examples of the X-ray imager include various types of apparatuses using X-rays, such as a dental CT apparatus, cephalo imaging apparatus and panoramic imaging apparatus.

According to another aspect of the invention, there is provided a scanner being removably mounted to an X-ray imager, wherein the X-ray imager comprises an X-ray beam generator for emitting an X-ray beam, an X-ray beam detector for detecting the X-ray beam to obtain an X-ray image of an object, and a body unit to which the X-ray beam generator and X-ray beam detector are mounted. The scanner comprises a scanner body to take an exterior image of the object, and a coupler being removably attached to the X-ray imager so that the scanner module is mounted to the X-ray imager.

The above X-ray imaging apparatus and three-dimensional scanner for the same according to the present invention have the following technical effects.

First, according to the present invention, an X-ray image and an exterior image of an object, e.g., a skull image and a face image may be obtained at the same time, thereby minimizing image adjustment procedures to superimpose those two images.

Second, according to the present invention, an X-ray image and an exterior image of an object (i.e., a patient) may be acquired while the patient remains stationary without changing posture or position, thereby avoiding inconvenience of the patient to obtain the X-ray image and exterior image.

Third, according to the present invention, the scanner is removably arranged on the X-ray imager so that it may be detached and independently used in a separate location or mounted to another different X-ray imager, thereby significantly enhancing usability.

Fourth, according to the present invention, the scanner is mounted to the X-ray imager so that the X-ray image and exterior image may be obtained alternatively or simultaneously, thereby allowing the operator to make choices with convenience.

BRIEF DESCRIPTION OF THE DRAWINGS

The features and advantages of the present invention may be more fully understood with reference to the embodiments of the invention taken in conjunction with the accompanying drawings, in which.

DETAILED DESCRIPTION OF THE PREFERRED EMBODIMENTS

Hereinafter, preferred embodiments of the present invention to achieve the above-described objects will be described with reference to the accompanying drawings. In the following description of the embodiments, the same terms or characters will be used to refer to the same elements, and additional or redundant explanations thereon will be omitted below.

First, one embodiment of an X-ray imaging apparatus according to the present invention, i.e., an X-ray imaging apparatus having a three-dimensional scanner will be described with reference to FIGS. 2 to 4.

Figure 1A:
FIGS. 1a and 1b show a teeth image and a skull image, respectively, which are examples of X-ray images taken by a generic dental X-ray imaging apparatus.
Figure 1B:
Figure 2:
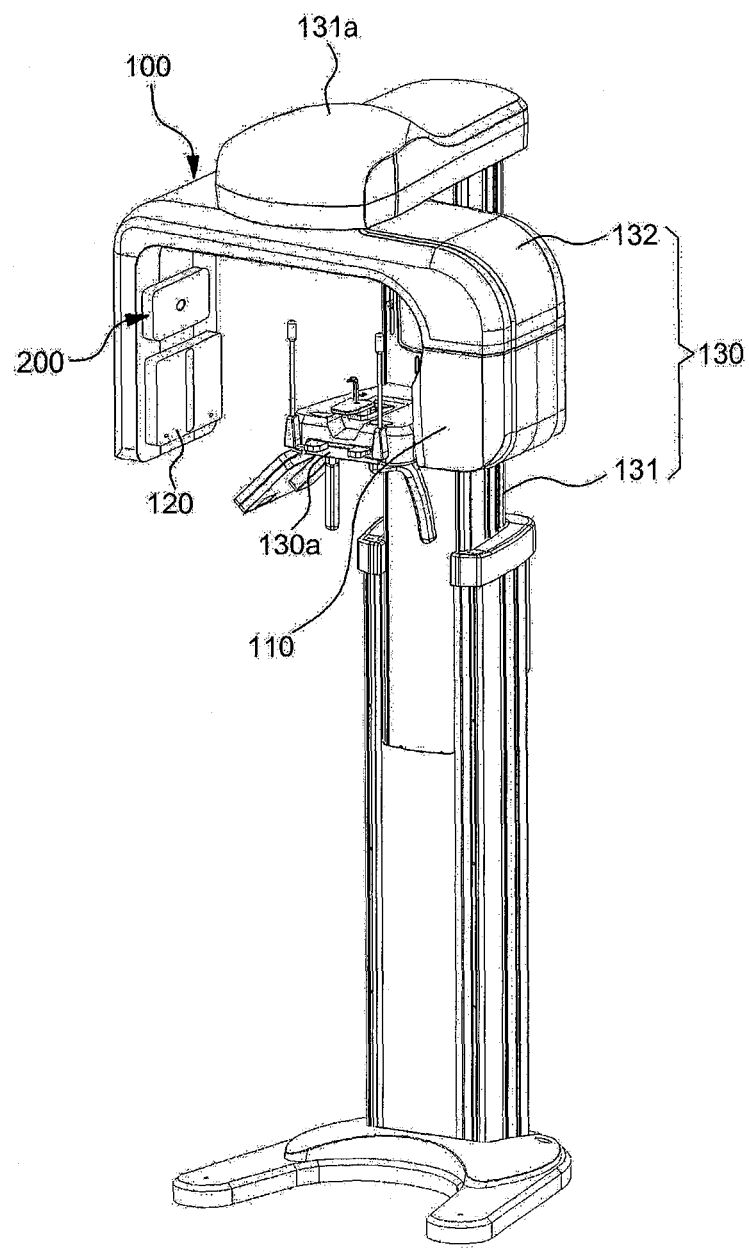
FIG. 2 is a perspective view showing one embodiment of an X-ray imaging apparatus according to the present invention, i.e., an X-ray imaging apparatus having a scanner.
Figure 3:
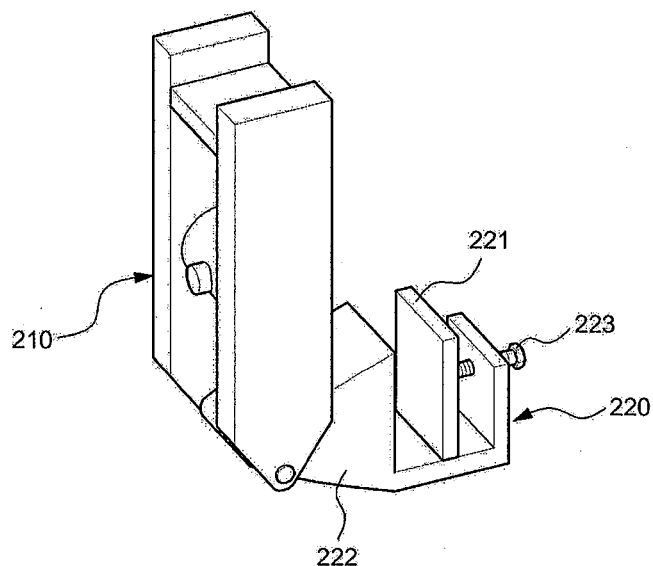
FIG. 3 is a perspective view showing one embodiment of a scanner of an X-ray imaging apparatus according to the present invention.
Figure 4:
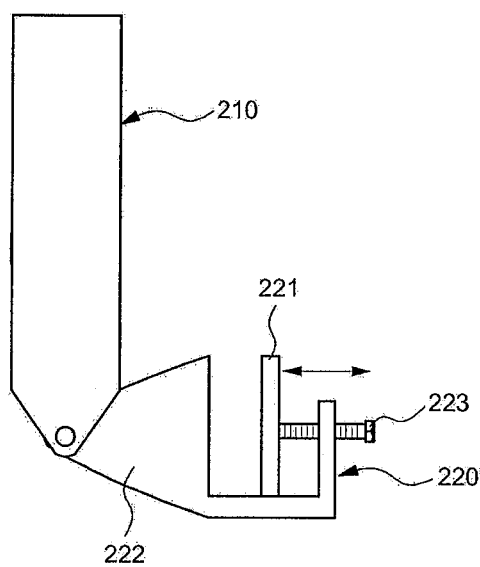
FIG. 4 is a side view showing a coupler of the scanner shown in FIG. 3.

Among the accompanying drawings, FIG. 2 is a perspective view showing one embodiment of an X-ray imaging apparatus according to the present invention, FIG. 3 is a perspective view showing one embodiment of a scanner of an X-ray imaging apparatus according to the present invention, and FIG. 4 is a side view showing a coupler of the scanner shown in FIG. 3.

Referring to FIGS. 2 to 4, one embodiment of an X-ray imaging apparatus according to the present invention comprises an X-ray imager 100 and a scanner (3D scanner) 200 mounted to the X-ray imager.

The X-ray imager 100 comprises an X-ray beam generator 110, an X-ray beam detector 120 and a body unit 130, wherein the X-ray beam detector 120 is installed opposite to the X-ray beam generator 110.

The X-ray beam generator 110 comprises an X-ray beam source for emitting an X-ray beam to take an X-ray image. Further, the X-ray beam detector 120 detects the X-ray beam to obtain an X-ray image, and more specifically detects the X-ray beam transmitted through an object to obtain an internal body image. Detailed principles and configurations of the X-ray beam generator 110 and X-ray beam detector 120 are known in the relevant art, and additional explanations thereon will be omitted.

Further, the body unit 130 comprises a base body 131 to support the weights of the X-ray beam generator 110 and X-ray beam detector 120, and a support body 132. Here, the X-ray beam generator 110 and X-ray beam detector 120 are installed to the support body 132. The support body 132 comprises a support arm arranged on the base body 131 so that it is supported by the base body 131. In the present embodiment, the base body 131 is in the form of a vertically elongated column, but the form is not limited thereto.

More specifically, the X-ray beam generator 110 is arranged at one end of the support body 132, i.e., the support arm, and the X-ray beam detector 120 is mounted to the other end of the support arm to face the X-ray beam generator 110. Accordingly, in this embodiment, the support arm 132, X-ray beam generator 110 and X-ray beam detector 120 together constitute an inverted U-shape.

Further, an alignment unit 130a is preferably arranged on the body unit 130 to place a man or woman's face in the proper position to obtain an X-ray image of an object, e.g., a head of a patient. When the jaw of the patient is placed on the alignment unit 130a, the head of the patient is aligned between the X-ray beam generator 110 and X-ray beam detector 120.

The support body 132, i.e., the support arm may be configured to rotate so that the X-ray beam generator 110 and X-ray beam detector 120 may circle around the object according to the rotation of the support body 132 and take an X-ray image of the object.

A drive box 131a (not shown) is arranged at the upper part of the base body to rotate the support body 132. The support body 132 is rotated by means of a rotation device such as a motor, gear and belt arranged within the drive box 131a.

Accordingly, when a face is placed between the X-ray beam generator 110 and X-ray beam detector 120 and then the support body 132 constituting an inverted U-shape together with the X-ray beam generator 110 and X-ray beam detector 120 is rotated by means of the rotation device, the X-ray beam generator 110 and X-ray beam detector 120 circle around the object facing each other and take an X-ray image of the object.

Examples of the X-ray imager include various types of apparatuses such as a dental CT apparatus, cephalo imaging apparatus and panoramic imaging apparatus, which use radioactive rays or X-rays to obtain internal body images.

Next, the scanner 200 is configured to obtain an. exterior image of an object. The scanner is arranged on the X-ray imager 100 and may be removably mounted to the X-ray imager 100.

The scanner 200 may be arranged on the X-ray beam generator 110 or the X-ray beam detector 120. The scanner 200 may also be arranged on the body unit 130, and more specifically on the support body 132, i.e., the support arm. Of course, the scanner 200 may also be arranged on the base body 131. Although not shown in the drawings, it may be rotatably arranged on the base body.

FIG. 2 shows that the scanner 200 is mounted to the support body 132, while it may be removably mounted to the support body as described above. One example of the element to removably mount the scanner 200 is a bolt. For example, a bolt is arranged as a rotating member in one of the scanner 200 and support body 132, and a hole for coupling of the bolt is arranged in the other one. This configuration may be diversely changed as long as the scanner may be removably attached to the support body 132.

Further, the scanner 200 may be applied as a three-dimensional (3D) scanner to obtain a three-dimensional image. Accordingly, an exterior image (e.g., a face image) of a patient may be obtained in three dimensions.

When the X-ray imager 100 takes an X-ray image, the scanner 200 may obtain an exterior image of an object at the same time. Otherwise, the X-ray imaging and exterior scanning may be sequentially performed. That is, according to the present invention, a face image and a cephalic X-ray image of a patient may be simultaneously obtained while the patient remains in one posture.

Referring to FIGS. 3 and 4, one embodiment of the scanner 200a is configured to removably attach to the X-ray imager, and comprises a scanner body 210 and a coupler 220. An imaging device (not shown) is arranged within the scanner body 210 to obtain an exterior image of the object. The coupler 220 is configured to fix the scanner body 210 to the X-ray imager 100.

The components such as the above imaging device and the like to obtain an exterior of an object are arranged in the scanner body 210. Detailed configurations and principles of the scanner to obtain images are generally known in the relevant art, and additional explanations thereon will be omitted.

The coupler 220 may be removably coupled to at least one of the X-ray imager 100 and scanner body 210. In the scanner 200a according to the present embodiment, one end of the coupler 220 is fixed to the scanner body 210 and the other end is removably coupled to the X-ray imager 100.

To this end, the coupler 220 comprises a chuck 221 and a coupler body 222, wherein the space of the chuck 221 may be adjusted to engage with a specific location of the X-ray imager, e.g., the X-ray beam generator 110. One end of the coupler body 222 is fixed to the scanner body, and the chuck 221 is arranged at the other end of the coupler body 222.

One example of the element to adjust the space of the chuck 221 is a screw adjuster 223, which may adjust the space as a screw rotates to move forward or backward in its axial direction.

Accordingly, when the space of the chuck 221 widens to put the X-ray beam generator 110 inside the chuck 221 and then narrows, the chuck 221 engages with the X-ray beam generator 110 so that the scanner body 210 is removably fixed to the X-ray beam generator 110. The scanner may be compatibly mounted to various forms of X-ray imagers. The scanner 200a may circle around an object according to the rotation of the support body 132 and obtain images of the object in various angles.

Of course, the coupler 220 should be mounted at the location that does not interfere with the X-ray beam emitted from the X-ray beam generator 110. The coupler 220 may also be coupled to the X-ray beam detector or another different location such as the support body 132. The configuration of the coupler 220 may be diversely changed according to the location where the scanner 200a is mounted. Further, the scanner body 210 may be rotatably coupled to the coupler 220.

Figure 5:
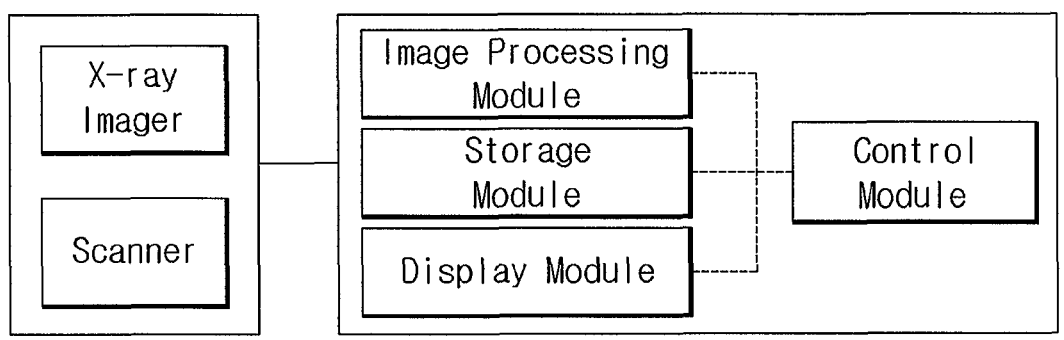
FIG. 5 is a block diagram showing one example of an image processing system equipped with an X-ray imaging apparatus according to the present invention.

FIG. 5 is a block diagram showing one example of an image processing system based on an X-ray imaging apparatus according to the present invention. The image processing system may comprise an image acquisition apparatus, i.e., an X-ray imaging apparatus having the above-described X-ray imager and scanner, as well as an image processing module to obtain the X-ray images and exterior images, a storage module to store the images, a display module to output the X-ray images and exterior images on a screen, and a control module.

Figure 6:
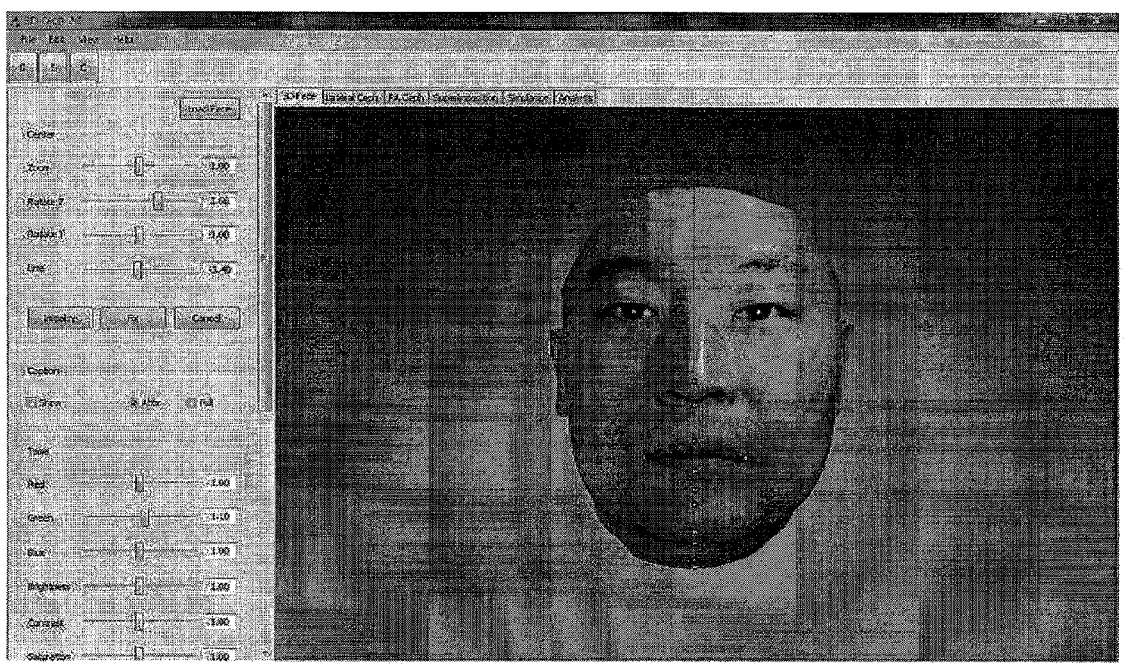
FIG. 6 is a picture showing an exterior image of an object (a face image) obtained by an X-ray imaging apparatus according to the present invention.
Figure 7:
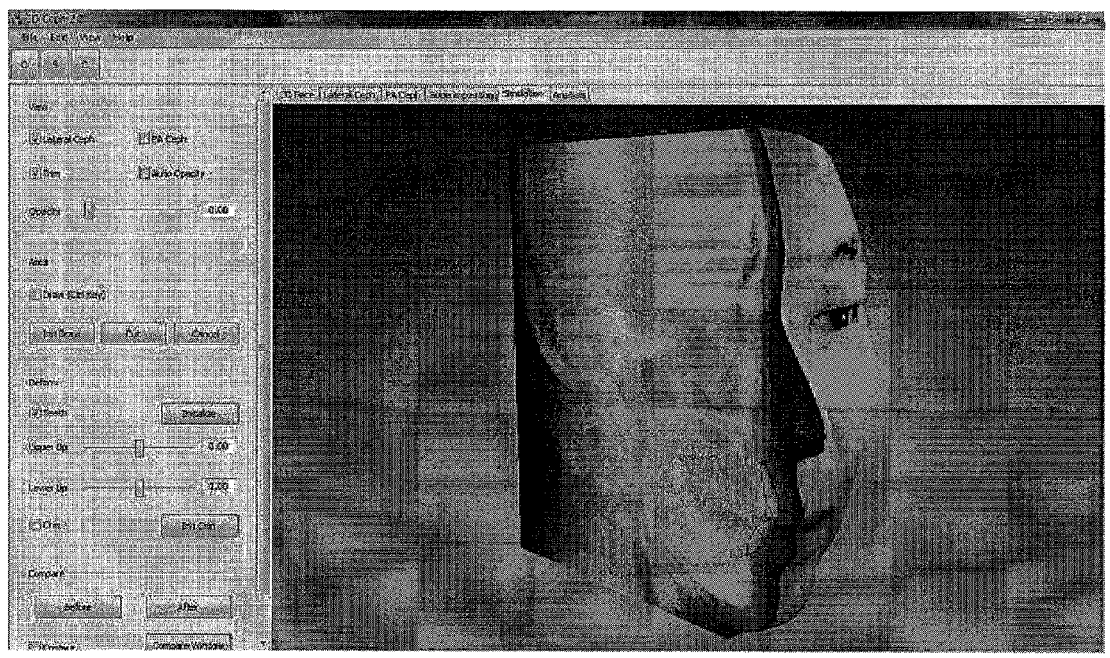
FIG. 7 is a picture showing one example of a superimposition image in which an exterior image of an object is superimposed with an X-ray image.

FIG. 6 is a picture showing a face image obtained by the scanner of the X-ray imaging apparatus, and FIG. 7 is a picture showing one example of a superimposition image in which an exterior image of an object (i.e., a face image) is superimposed with an X-ray image.

Hereinafter, other embodiments of an X-ray imaging apparatus according to the present invention will be described with reference to FIGS. 8 and 9.

Figure 8:
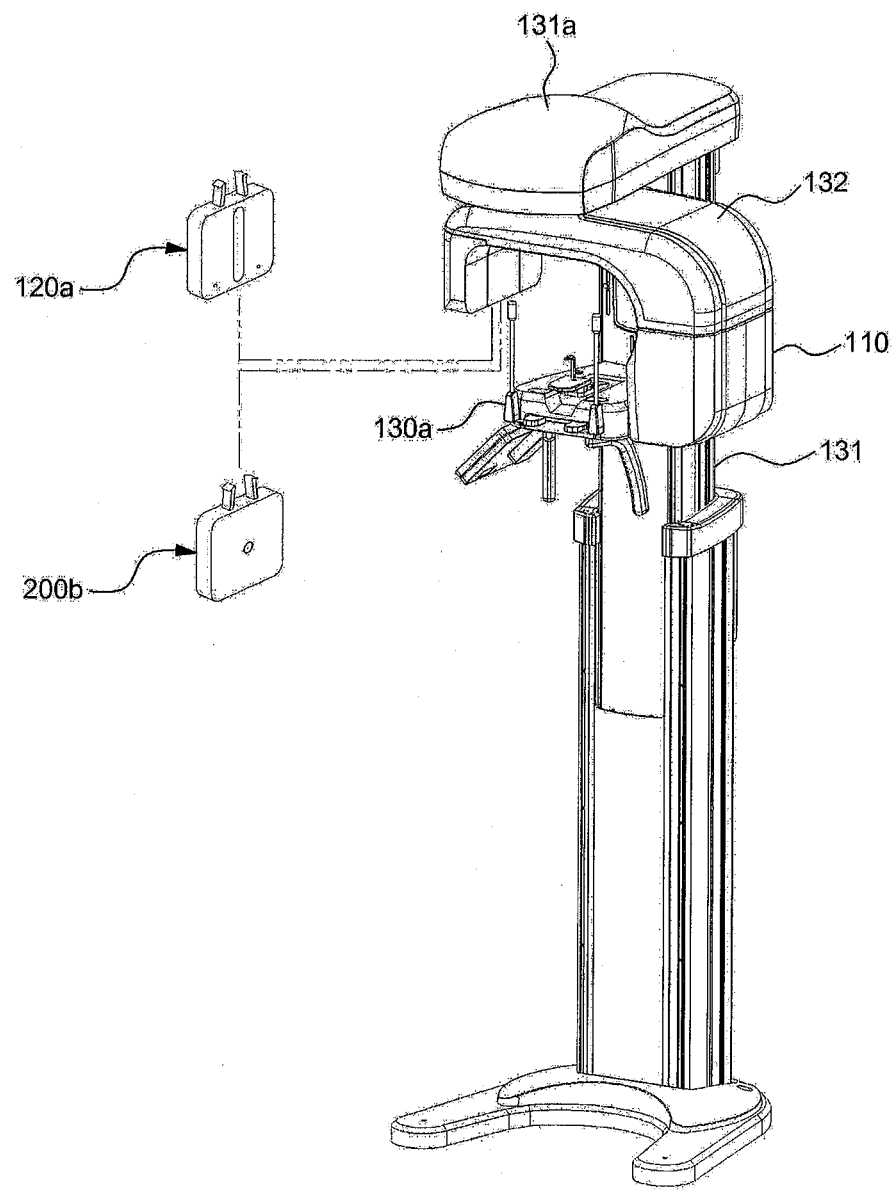
FIG. 8 is a perspective view showing another embodiment of an X-ray imaging apparatus according to the present invention.

Referring to FIG. 8, in another embodiment of an X-ray imaging apparatus according to the present invention, a scanner 200b is replaceably mounted at the location where an X-ray beam detector 120a is mounted. The X-ray beam detector 120a is removably mounted to the support arm 132 so that it may be detached from the support arm 132 and the scanner 200b may be mounted taking the place of the X-ray beam detector 120a.

The mounting configurations of the X-ray beam generator 120a and scanner 200b may employ the same elements, e.g., a variety of known coupling elements such as hooks and screws.

Figure 9:
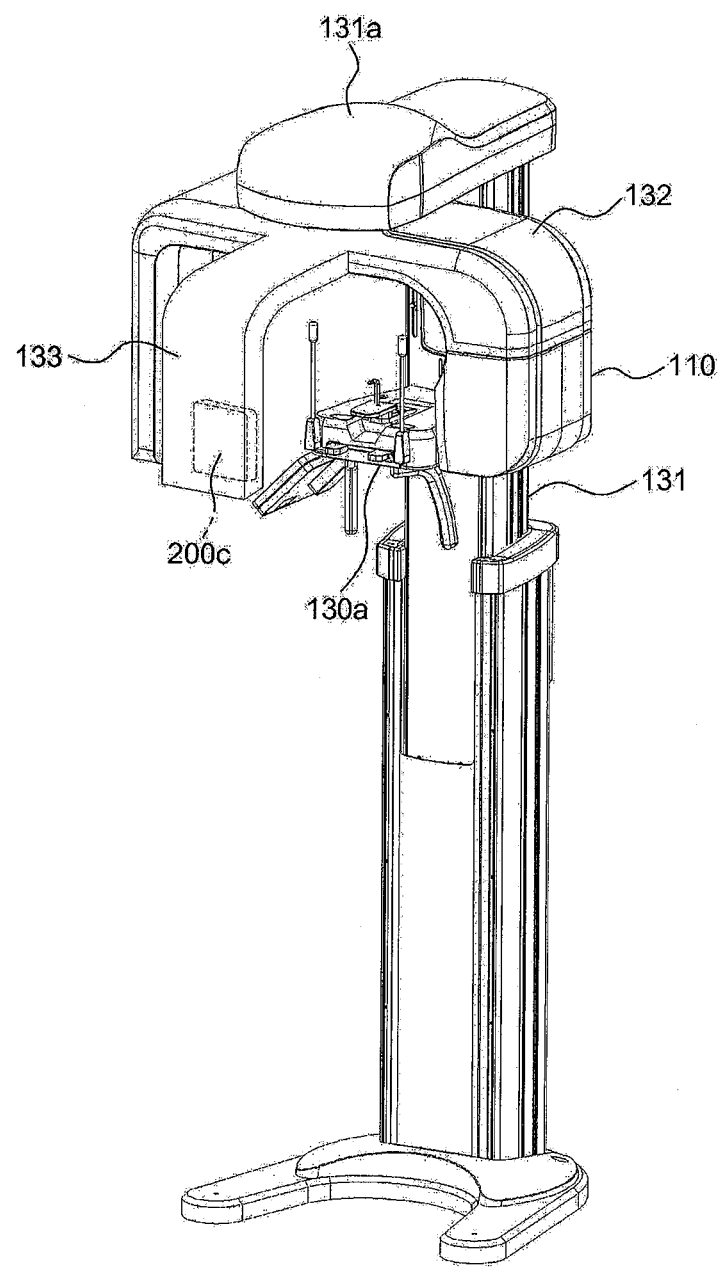
FIG. 9 is a perspective view showing yet another embodiment of an X-ray imaging apparatus according to the present invention.

Next, referring to FIG. 9, in yet another embodiment of an X-ray imaging apparatus according to the present invention, a scanner 200c is supported by the support arm 132. More specifically, the scanner 200c is mounted to a scanner arm 133 arranged on the support arm 132 so that it may be coupled to the support arm 132 via the scanner arm 133.

In the present embodiment, the scanner arm 133 is formed in a generally right-angled shape, and may be removably mounted to the support arm 132. The scanner 200c may be removably coupled to the scanner arm 133. The scanner arm 133 may also be directly arranged on the base body.

While the preferred embodiments of the present invention have been described as above, it will be apparent to those skilled in the art that the present invention may be embodied in other specific forms without departing from the spirit or scope of the invention.

Therefore, the above-described embodiments should be regarded as illustrative rather than restrictive, and thus the present invention is not limited to the above description and may be modified within the scope of the appended claims and their equivalents.

What is claimed is:

1. An X-ray imaging apparatus, comprising:
   an X-ray imager comprising an X-ray beam generator for emitting an X-ray beam, an X-ray beam detector for detecting the X-ray beam to obtain an X-ray image of an object, and a body unit to which the X-ray beam generator and X-ray beam detector are mounted; and
   a scanner being arranged on the X-ray imager to obtain an exterior image of the object.

2. The X-ray imaging apparatus of claim 1, wherein the scanner is removably mounted to the X-ray imager.

3. The X-ray imaging apparatus of claim 2, wherein the scanner comprises:
   a scanner body to take the exterior image of the object; and
   a bracket to fix the scanner body to the X-ray imager.

4. The X-ray imaging apparatus of claim 3, wherein the bracket is removably coupled to at least one of the X-ray imager and scanner body.

5. The X-ray imaging apparatus of claim 1, wherein the body unit comprises a base body to support the weights of the X-ray beam generator and X-ray beam detector, and a support arm arranged on the base body to which the X-ray beam generator and X-ray beam detector are installed.

6. The X-ray imaging apparatus of claim 5, wherein the scanner is supported by the support arm.

7. The X-ray imaging apparatus of claim 6, wherein the X-ray beam detector is removably mounted to the support arm, and the scanner is capable of being removably installed at the location where the X-ray beam detector is mounted.

8. The X-ray imaging apparatus of claim 5, wherein the body unit further comprises a scanner arm to which the scanner is mounted, and the scanner arm is arranged on the support arm or the base body.

9. The X-ray imaging apparatus of claim 5, wherein the support arm is capable of rotating around the object.

10. A scanner being removably mounted to an X-ray imager, wherein the X-ray imager comprises an X-ray beam generator for emitting an X-ray beam, an is X-ray beam detector for detecting the X-ray beam to obtain an X-ray image of an object, and a body unit to which the X-ray beam generator and X-ray beam detector are mounted, and wherein the scanner comprises a scanner body to take an exterior image of the object, and a bracket being removably attached to the X-ray imager so that the scanner module is mounted to the X-ray imager.

* * * * *